United States Patent [19]

Wada et al.

[11] Patent Number: 4,578,507
[45] Date of Patent: Mar. 25, 1986

[54] PROCESS FOR THE PRODUCTION OF CINNAMIC ACID ESTERS

[75] Inventors: Keisuke Wada, Yokohama; Yoshimitsu Kobayashi, Tokyo; Yukio Kasori, Yokohama, all of Japan

[73] Assignee: Mitsubishi Chemical Industries Limited, Tokyo, Japan

[21] Appl. No.: 694,211

[22] Filed: Jan. 24, 1985

[30] Foreign Application Priority Data

Feb. 10, 1984 [JP] Japan .................................. 59-23837

[51] Int. Cl.$^4$ ............................................. C07C 69/76
[52] U.S. Cl. .................................................. 560/104
[58] Field of Search ........................ 560/104; 562/406

[56] References Cited

U.S. PATENT DOCUMENTS 3,313,843  4/1967  Maulihan ........................... 560/104
3,530,168  9/1970  Biale ................................... 560/104

FOREIGN PATENT DOCUMENTS 7021342  4/1982  Japan .................................. 560/104

Primary Examiner—Paul J. Killos
Attorney, Agent, or Firm—Jordan B. Bierman

[57] ABSTRACT

A process for the production of cinnamic acid esters which is characterized by reacting a styrene with an aliphatic alcohol of 1–4 carbon atoms, carbon monoxide and oxygen in the presence of a catalyst comprising (a) a palladium metal or a compound thereof, (b) a salt of copper or iron, (c) a salt of an alkali metal or an alkaline earth metal, (d) an organic acid and (e) a halogen compound.

1 Claim, 2 Drawing Figures

PROCESS FOR THE PRODUCTION OF CINNAMIC ACID ESTERS

BACKGROUND OF THE INVENTION

1. Field of the Invention

This invention relates to a process for the production of cinnamic acid esters. More specifically, it relates to a process for the production of cinnamic acid esters which comprises oxidatively carboxylating a styrene in the presence of an alcohol.

2. Description of the Prior Art

Cinnamic acid is used not only as a perfume starting material together with cinnamic aldehyde, cyclamen aldehyde, β-amylcinnamic aldehyde etc. but also as a starting material for agricultural chemicals, and, on a laboratory basis, this may be produced by Perkin reaction.

The process for the production of cinnamic acid esters by the oxidative carbonylation of styrene is disclosed in, for example, Japanese Patent Application Laid-open Nos. 40709/1978, 15242/1981, 22749/1981, 22750/1981, 71039/1981, 21342/1982, 21343/1982, 70836/1982 etc.

In Japanese Patent Application Laid-open No. 15242/1981, there is used a catalyst comprising (1) a platinum group metal or a compound thereof, (2) a copper salt or an iron salt and (3) an organic acid salt of a metal selected from alkali metals, alkaline earth metals and aluminum group metals.

Japanese Patent Application Laid-open No. 70836/1982 discloses a catalyst system comprising (1) a platinum group metal or a salt thereof, (2) a salt of copper or iron, (3) one or more compounds selected from hydroxides, carbonates and acetates of alkali metals and alkaline earth metals in an ethylene glycol-ether based solvent.

Furthermore, Japanese Patent Application Laid-open No. 49709/1978 relates to the oxidative carbonylation reaction, which is the reaction mode in the present invention, but in the examples of said application, the selectivity to unsaturated carboxylic acid esters is extremely low and the catalyst in said system is composed of a solid catalyst of a group VIII noble metal single substance supported on a support.

SUMMARY OF THE INVENTION

The present inventors have been intensively studying on an industrially advantageous process for the production of cinnamic acid esters, that is, a process for the production of cinnamic acid esters by the oxidative carbonylation of a styrene and, as a result, have discovered the fact that by contacting a styrene, an aliphatic alcohol of 1–4 carbon atoms, carbon monoxide and oxygen in the presence of a catalyst comprising (a) a palladium metal or a compound thereof, (b) a salt of copper or iron, (c) a salt of an alkali metal or an alkaline earth metal, (d) an organic acid and (e) a halogen compound, a cinnamic acid ester may be produced with extremely high activity and also with a long life, thereby having accomplished this invention.

In other words, the features of the catalyst system of this invention are, as will be made clear from the examples described hereinlater, such that as compared with the catalyst systems described in Japanese Patent Application Laid-open No. 15242/1981, where the catalyst concentrations are the same, the production rate of a cinnamic acid ester is relatively considerably enhanced at a generally optimum reaction temperature, i.e., a reaction temperature of about 80°–140° C., and, in addition, that by further containing an organic acid as a constituting component of the catalyst, the catalyst life is improved and thus a stalbe reaction is enabled for a prolonged time. Such a fact is completely beyond expectation from the catalyst systems described in Japanese Patent Application Laid-open Nos. 15242/1981, 70836/1982 etc., and this has been made possible for the first time by a catalyst system of this invention which comprises (a) a palladium metal or a compound thereof, (b) a salt of copper or iron, (c) a salt of an alkali metal or an alkaline earth metal, (d) an organic acid and (e) a halogen compound.

DETAILED DESCRIPTION OF THE PREFERRED EMBODIMENTS

Figure 1:
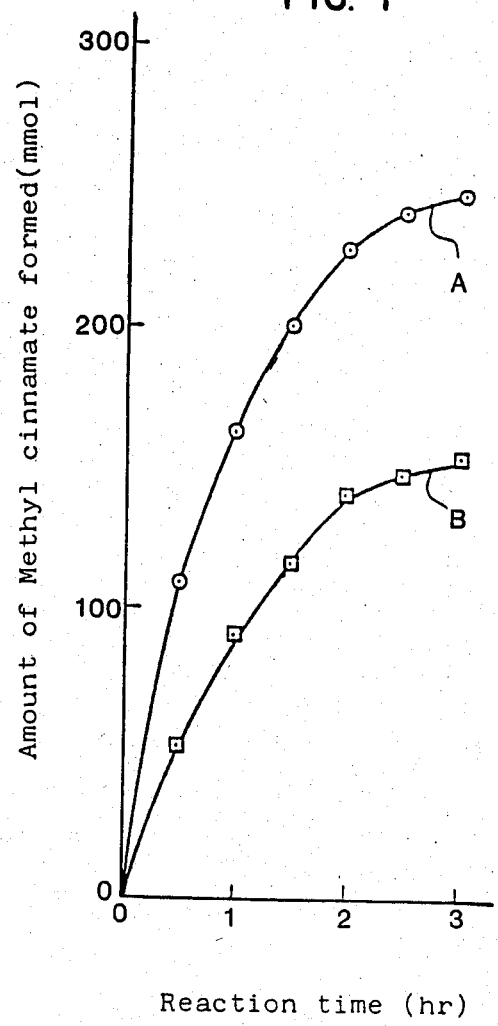
FIG. 1 and FIG. 2 are graphs showing the amounts of methyl cinnamate formed at certain intervals in the reaction of this invention. The ordinate axis indicates the amount of methyl cinnamate formed (mmol) and the abscissa axis indicates the reaction time (hr). In the figures, A is for Example 4, B for Comparative Example 2, C for Example 5, and D for Comparative Example 3.

The starting materials used in the process of this invention are a styrene of the formula:

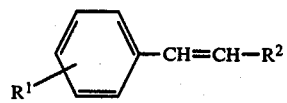

wherein $R^1$ represents hydrogen, halogen, alkyl of 1–4 carbon atoms or alkoxy of 1–4 carbon atoms and $R^2$ represents hydrogen or alkyl of 1–6 carbon atoms; an aliphatic alcohol of 1–4 carbon atoms, carbon monoxide and oxygen.

Specific examples of the styrene include styrene, β-methylstyrene, p-methylstyrene, p-methoxystyrene, p-chlorostyrene, β-methyl-p-isopropylstyrene, β-amylstyrene etc.

Specific examples of the aliphatic alcohol of 1–4 carbon atoms include methanol, ethanol, isopropyl alcohol, n-butyl alcohol, t-butyl alcohol etc., and, in addition, compounds which can dissociate in the reaction system and liberate the above-described alcohols may be used, for example, acetals, ketals, carboxylic acid orthoesters, dialkoxycycloalkanes, orthoboric acid esters.

The carbon monoxide and the oxygen may be used in a neat form, or they may be used by diluting with an inert gas such as nitrogen, argon etc.

The reaction by the process of this invention is effected in the presence of a catalyst which comprises (a) a palladium metal or a compound thereof, (b) a slat of copper or iron, (c) a salt of an alkali metal or an alkaline earth metal, (d) an organic acid and (e) a halogen compound.

Examples of the palladium include metal palladium such as palladium black, supported metal palladium etc., zero-valent palladium complexes such as tetrakis(triphenylphosphine) palladium etc., divalent palladium inorganic salts such as palladium chloride, palladium nitrate etc., divalent palladium carboxylic acid salts such as palladium acetate, palladium benzoate etc., and divalent palladium complexes such as bis- (acetylacetonato)palladium, bis(triphenylphosphine)-dichloropalladium etc. Where these palladium catalysts are used by supporting on a support, for example, silica, alumina, silica-aluminina, magnesia, titania, diatomaceous earth, active carbon, graphite, barium carbonate, calcium carbonate etc. may be used as supports.

Of the salts of copper or iron, examples of the organic acid salt include acetates, propionates, butyrates, stearates, benzoates etc., and, in particular, the acetates are effective. Further, examples of the halide of copper or iron include cupric chloride etc.

Examples of the halide of an alkali metal or an alkaline earth metal include lithium chloride, sodium chloride, calcium chloride, barium chloride, barium bromide, barium iodide etc., and examples of the organic acid salt include acetates etc.

Examples of the organic acid which is one of the catalyst components include aliphatic and aromatic carboxylic acids such as acetic acid, propionic acid, butyric acid, stearic acid, benzoic acid etc., and of those, the aliphatic carboxylic acids, especially acetic acid, are suitable.

Examples of the halogen compound include chlorides, bromides, iodides etc.; although it may be omitted by using a halide for any of the catalyst components (a)-(c), it may be added as a halogen compound independently from the components (a)-(c). Examples of such a halogen compound include hydrogen chloride, halogenoammonium salts such as tetramethylammonium chloride, tetra-n-butylammonium bromide, pyridine hydrochloride, ammonium chloride etc., halogenophosphonium or arsonium salts such as tetramethylphosphonium iodide, tetraethylphosphonium bromide, tetra-n-butylphosphonium chloride, tetraphenylphosphonium bromide, tetraphenylarsonium chloride etc., bistriphenylphosphinium chloride, bistriphenylphosphinecarbenium chloride etc.

Although the effect exerted by the organic acid added according to this invention is not fully clarified, it is presumed that the salt of copper or iron undergoes hydrolysis by the water produced by the reaction, thereby preventing the reduction in the catalyst activity.

The proportions of the respective components used as the catalyst are suitably such that the atomic ratio of the palladium metal or a compound thereof to the salt of copper or iron be in the range of 1 to 1–5,000, preferably 1 to 5–500.

Further, the molar ratio of the salt of copper or iron to the salt of an alkali metal or an alkaline earth metal is suitably in the range of 1 to 0.01–100, preferably 1 to 0.1–10.

On the other hand, the molar ratio of the salt of copper or iron to the organic acid is suitably in the range of 1 to 0.1–500, preferably 1 to 1–50.

The molar ratio of the salt of copper or iron to the halogen compound is suitably in the range of 1 to 0.00001–100, preferably 1 to 0.0001–10.

The use of the organic acid in this invention exerts an effect to prolong the catalyst life, and where the reaction is effected in a batchwise mode, it may also be added to the reaction system in the second or subsequent run, or where the reaction is effected in a continuous manner, it may also be added thereto in the middle of course.

On carrying out the process of this invention, while the reaction solvent is not particularly required, an appropriate inert solvent may be used in some cases to smoothly conduct the operation. Specific examples of such a solvent include ethers such as diethyl ether, diphenyl ether, dioxane, tetrahydrofuran, ethylene glycol dimethyl ether etc., ketones such as acetone, methyl ethyl ketone, dibutyl ketone, acetophenone etc., esters such as methyl acetate, ethyl acetate, ethyl propionate, benzyl benzoate, dimethyl phenylsuccinate etc., aromatic hydrocarbons such as benzene, toluene, p-xylene, ethylbenzene etc., aliphatic or alicyclic hydrocarbons such as n-hexane, n-octane, cyclohexane etc., amides such as acetamide, N-methylpyrrolidone etc. and carbonates such as ethylene carbonate, propylene carbonate etc.

For selecting the reaction temperature, although the yield of the cinnamic acid ester can be enhanced by raising the reaction temperature in the process of this invention, if it is too high, on the contrary, the selectivity to the cinnamic acid ester is decreased owing to occurence of side reactions such as carbon dioxide generation etc., and therefore, the reaction temperature is suitably in the range of normal temperature to 200° C., preferably 60°–160° C.

The reaction mixture obtained by carrying out the process of this invention may then be treated by conventional separating means such as distillation, extraction etc., thereby the cinnamic acid ester may be separated and obtained.

This invention is more particularly described by the following examples, but it should be understood that this invention is not restricted to these examples unless it departs from the spirit and scope of the invention.

In the examples, the selectivity to methyl cinnamate means the selectivity given below:

$$\text{Selectivity (\%)} = \frac{\text{(Methyl Cinnamate)}}{\text{(Methyl Cinnamate)} + \text{(Benzaldehyde)} + \text{(Acetophenone)} + \text{(Methyl 2- or 3-propionate)} + \text{(Dimethyl Phenylsuccinate)}} \times 100$$

EXAMPLE 1

Into a spinner stirring type glass inner-cylinder Hastelloy C autoclave of a capacity of 90 ml were charged 7 ml of styrene, 3 ml of methanol, 2% Pd/A.C. (2% by weight of palladium supported on active carbon) in an amount of 0.05 mmol as Pd, 0.5 mmol of cupric acetate, 0.5 mmol of barium chloride and 1.0 mmol of acetic acid, and after tightly closing, carbon monoxide was introduced under pressure to 8.0 kg/cm$^2$G. Then, 6% $O_2/N_2$ (nitrogen gas containing 6% by volume of oxygen) was introduced under pressure to make the total pressure 102.5 kg/cm$^2$G at room temperature. The autoclave was heated in an electric oven, and the reaction was effected at 120° C. for 30 minutes. After the completion of the reaction, the autoclave was cooled with water, then the pressure was released, and the composition of the reaction gas and the composition of the reaction mixture were analyzed by gas chromatography.

As a result, the methyl cinnamate formed was 10.34 mmol, the carbon dioxide was 1.34 mmol, and the selectivity to methyl cinnamate was 88.21%.

EXAMPLE 2

The reaction and analysis were conducted under the same conditions as in Example 1 except that the 1.0 mmol of the acetic acid in Example 1 was changed to 3.0 mmol.

The methyl cinnamate formed was 12.08 mmol, the carbon dioxide was 1.82 mmol, and the selectivity to methyl cinnamate was 84.87%.

EXAMPLE 3

The reaction and analysis were conducted under the same conditions as in Example 1 except that the 1.0 mmol of the acetic acid in Example 1 was changed to 17.5 mmol.

The methyl cinnamate formed was 10.26 mmol, the carbon dioxide was 2.57 mmol, and the selectivity to methyl cinnamate was 71.07%.

COMPARATIVE EXAMPLE 1

The reaction and analysis were conducted under the same conditions as in Example 1 except that the 1.0 mmol of the acetic acid in Example 1 was omitted.

The methyl cinnamate formed was 9.81 mmol, the carbon dioxide was 2.83 mmol, and the selectivity to methyl cinnamate was 89.53%.

EXAMPLE 4

Into a Teflon inner-cylinder Hastelloy C autoclave of a capacity of 300 ml and equipped with a magnetic induction rotating stirrer, a reflux condenser, a gas inlet pipe and a liquid withdrawal pipe were charged 0.5% Pd/A.C. (0.5% by weight of palladium supported on active carbon) in an amount of 0.05 mmol as Pd, 20 mmol of cupric acetate, 20 mmol of barium chloride, 160 mmol of acetic acid, 70 ml of styrene and 30 ml of methanol, then, a mixed gas of nitrogen/oxygen/carbon monoxide (84.9/5.6/9.5 in volume ratio) was introduced to make the pressure inside the reaction system 20.0 kg/cm$^2$G, and while maintaining this pressure and passing the mixed gas at a gas flow rate at the reactor outlet of 34.1 Nl/hr, the reaction temperature was gradually raised to 120° C. While passing the mixed gas under the same conditions, the reaction was effected for 3 hours. Very small amounts of the reaction mixture were withdrawn at 30 minutes' intervals and analyzed by gas chromatography, and also the gas composition was analyzed at the same intervals by subjecting a part of the gas phase coming out of the reflux condenser to gas chromatography. The amounts of methyl cinnamate formed at intervals are shown in FIG. 1.

COMPARATIVE EXAMPLE 2

The reaction and analysis were conducted under conditions similar to those in Example 4 except that the acetic acid was not charged. The results are shown in FIG. 1.

EXAMPLE 5

Figure 2:
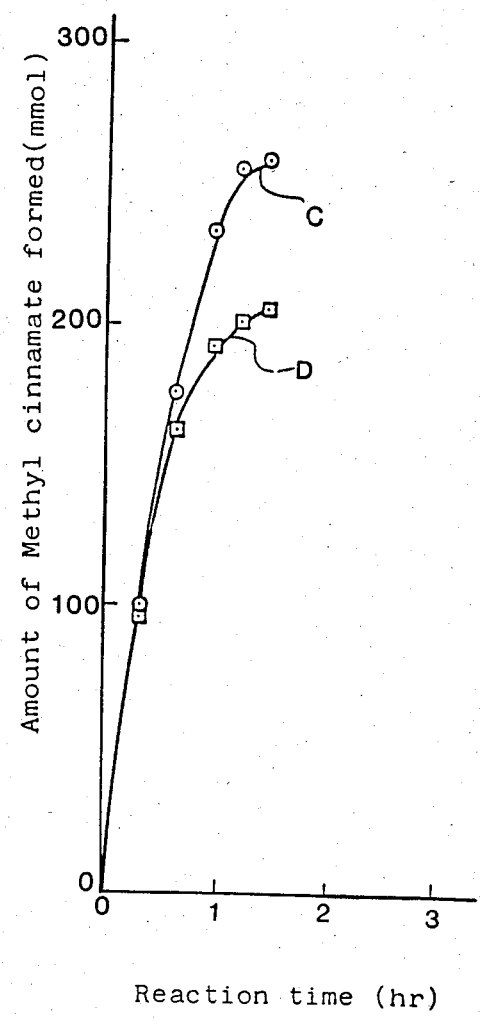

Into the same autoclave as that used in Example 4 were charged 2% Pd/A.C. in an amount of 0.5 mmol as Pd, 20 mmol of cupric acetate, 20 mmol of barium chloride, 160 mmol of acetic acid, 70 ml of styrene and 30 ml of methanol, then, a mixed gas of nitrogen/oxygen/carbon monoxide (86.0/5.5/8.5 in volume ratio) was introduced to make the pressure inside the reaction system 20.0 kg/cm$^2$G, and while maintaining this pressure and passing the mixed gas at a gas flow rate at the reactor outlet of 76.6 Nl/hr, the reaction was effected for 1.5 hours while maintaining the reaction temperature at 120° C. The amounts of methyl cinnamate formed at intervals are shown in FIG. 2.

COMPARATIVE EXAMPLE 3

The reaction and analysis were conducted under conditions similar to those in Example 5 except that the acetic acid was not charged. The results are shown in FIG. 2.

EXAMPLE 6

Into a Teflon inner-cylinder Hastelloy C autoclave of a capacity of 300 ml and equipped with a magnetic induction rotating stirrer, a reflux condenser, a gas inlet pipe and a liquid withdrawal pipe were charged 2% Pd/A.C. (2% by weight of palladium supported on active carbon) in an amount of 0.5 mmol as Pd, 5.0 mmol of cupric acetate, 5.0 mmol of barium chloride, 70 ml of styrene and 30 ml of methanol, then, a mixed gas of nitrogen/oxygen/carbon monoxide (86.3/5.3/8.4 in volume ratio) was introduced to make the pressure inside the reaction system 50.0 kg/cm$^2$G, and while maintaining this pressure and passing the mixed gas at a gas flow rate at the reactor outlet of 34.5 Nl/hr, the reaction was effected for 3 hours while maintaining the reaction temperature at 100° C. As the result of analysis of the liquid and the gas after the reaction by gas chromatography, the amount of methyl cinnamate formed was 168.2 mmol, the amount of carbon dioxide formed was 73.2 mmol, and the selectivity to methyl cinnamate was 75.3%. The reaction mixture containing this catalyst removed from the autoclave was left at room temperature for several hours, and thereafter the solid catalyst component was recovered by suction filtration.

This solid catalyst component weighed 4.68 g after drying at 80° C. for a whole day and night.

One tenth of the thus obtained solid catalyst component i.e. 0.468 g thereof was charged into a spinner stirring type glass inner-cylinder Hastelloy C autoclave of a capacity of 90 ml together with 3.0 mmol of acetic acid, 7 ml of styrene and 3 ml of methanol, and, after tightly closing, carbon monoxide was introduced under pressure to 8.0 kg/cm$^2$G. Thereafter, 6% O$_2$/N$_2$ (nitrogen gas containing 6% by volume of oxygen) was introduced under pressure to make the total pressure 102.5 kg/cm$^2$G at room temperature. The autoclave was heated in an electric oven, and the reaction was effected for 30 minutes while maintaining at 120° C. After the completion of the reaction, the autoclave was cooled with water, then the pressure was released, and the composition of the reaction gas and the composition of the reaction mixture were analyzed by gas chromatography.

As a result, the methyl cinnamate formed was 9.88 mmol, the carbon dioxide was 1.01 mmol, and the selectivity to methyl cinnamate was 86.21%.

EXAMPLES 7-9 and COMPARATIVE EXAMPLE 4

The reactions and analyses were conducted under the same conditions as in Example 6 except that the 3.0 mmol of the acetic acid was changed to the amounts set forth in the following Table 1. The results are shown in the same table.

TABLE 1

| Example | Amount of Acetic Acid Used (mmol) | Reaction Products | | Selectivity to Methyl Cinnamate (%) |
|---|---|---|---|---|
| | | Carbon Dioxide (mmol) | Methyl Cinnamate (mmol) | |
| Example 7 | 2.0 | 1.04 | 6.27 | 73.66 |
| Example 8 | 1.0 | 0.86 | 4.79 | 66.26 |
| Example 9 | 0.6 | Almost None | 4.00 | 68.69 |
| Comparative Example 4 | — | Almost None | 0.64 | 73.48 |

EXAMPLE 10

Into a Teflon inner-cylinder Hastelloy C autoclave of a capacity of 300 ml and equipped with a magnetic induction rotating stirrer, a reflux condenser, a gas inlet pipe and a liquid withdrawal pipe were charged 5% Pd/A.C. in an amount of 0.5 mmol as Pd, 5.0 mmol of cupric acetate, 5.0 mmol of barium chloride, 70 ml of styrene and 30 ml of methanol, then, a mixed gas of nitrogen/oxygen/carbon monoxide (86.8/5.5/7.7 in volume ratio) was introduced to make the pressure inside the reaction system 50.0 kg/cm$^2$G, and while maintaining this pressure and passing the mixed gas at a gas flow rate at the reactor outlet of 34.2 Nl/hr, the reaction was effected for 3 hours while maintaining the reaction temperature at 100° C. In this system, 111.9 mmol of methyl cinnamate and 48.7 mmol of carbon dioxide had been formed. On the other hand, the selectivity to methyl cinnamate was 73.7%. The reaction mixture (composed of an ununiform phase) containing the catalyst removed from the autoclave was left at room temperature for several hours, and the solid catalyst component was recovered by suction filtration.

This solid catalyst component weighed 2.52 g after drying at 80° C. for a whole day and night.

One tenth of the thus obtained solid catalyst component, i.e., 0.252 g thereof was charged into a spinner stirring type glass inner-cylinder Hastelloy C autoclave of a capacity of 90 ml together with 3.0 mmol of acetic acid, 7 ml of styrene and 3 ml of methanol, and, after tightly closing, carbon monoxide was introduced under pressure to 8.0 kg/cm$^2$G. Thereafter, 6% O$_2$/N$_2$ gas was introduced under pressure to make the total pressure 102.5 kg/cm$^2$G at room temperature. The autoclave was heated in an electric oven, and the reaction was effected for 30 minutes while maintaining at 120° C. As a result, the methyl cinnamate formed was 9.14 mmol, the carbon dioxide was 2.28 mmol, and the selectivity to methyl cinnamate was 80.32%.

EXAMPLE 11

The reaction and analysis were conducted under the same conditions as in Example 10 except that the 3.0 mmol of the acetic acid was changed to 17.5 mmol of acetic acid. As a result, the amount of methyl cinnamate formed was 8.81 mmol, the carbon dioxide was 0.99 mmol, and the selectivity to methyl cinnamate was 77.21%.

COMPARATIVE EXAMPLE 5

The reaction and analysis were conducted under the same conditions as in Example 10 except that the 3.0 mmol of the acetic acid was not charged, to find that the amount of methyl cinnamate formed was 0.05 mmol, the carbon dioxide had not been formed, and the selectivity to methyl cinnamate was 25.90%.

EXAMPLES 12-14 and COMPARATIVE EXAMPLE 6

The reactions and analyses were conducted under conditions similar to those in Example 1 except that the cupric acetate used in Example 1 was replaced by barium acetate, the total pressure of the reaction system was changed to 103 kg/cm$^2$G and the amount of the acetic acid used was changed to the amounts set forth in Table 2. The results are shown in Table 2.

TABLE 2

| Example | Amount of Acetic Acid Used (mmol) | Reaction Products | | Selectivity to Methyl Cinnamate (%) |
|---|---|---|---|---|
| | | Carbon Dioxide (mmol) | Methyl Cinnamate (mmol) | |
| Example 12 | 1.0 | 1.02 | 10.15 | 86.2 |
| Example 13 | 3.0 | 1.53 | 10.38 | 80.31 |
| Example 14 | 17.5 | 1.79 | 10.58 | 75.44 |
| Comparative Example 6 | — | 2.60 | 9.11 | 84.67 |

EXAMPLE 15

Into a spinner stirring type glass inner-cylinder Hastelloy C autoclave of a capacity of 90 ml were charged 5 ml of styrene, 5 ml of methanol, 0.05 mmol of palladium chloride, 0.5 mmol of cupric acetate, 0.5 mmol of barium acetate and 1.0 mmol of acetic acid, and after tightly closing, carbon monoxide was introduced under pressure to 8.0 kg/cm$^2$G. Then, 6% O$_2$/N$_2$ (nitrogen gas containing 6% by volume of oxygen) was introduced under pressure to make the total pressure 102.5 kg/cm$^2$G at room temperature. The autoclave was heated in an electric oven, and the reaction was effected at 120° C. for 30 minutes. After the completion of the reaction, the autoclave was cooled with water, then the pressure was released, and the composition of the reaction gas and the composition of the reaction mixture were analyzed by gas chromatography.

As a result, the methyl cinnamate formed was 11.3 mmol, the carbon dioxide was 2.7 mmol, and the selectivity to methyl cinnamate was 87.7%.

What is claimed is:

1. A process for the production of cinnamic acid esters which is characterized by reacting a styrene with an aliphatic alcohol of 1-4 carbon atoms, carbon monoxide and oxygen in the presence of a catalyst comprising (a) a palladium metal or a compound thereof, (b) a salt of copper or iron, (c) a salt of an alkali metal or an alkaline earth metal, (d) an organic acid and (e) a halogen compound.

* * * * *